(12) United States Patent
Kerr et al.

(10) Patent No.: US 8,912,320 B2
(45) Date of Patent: *Dec. 16, 2014

(54) PROCESS FOR REMOVING DIMETHYLAMINE

(75) Inventors: John Kerr, South Croydon (GB); Robert Jansen, Portela LRS (PT); Anthony Baiada, Dagenham (GB); Duane Leinhos, Satsuma, AL (US); James Edwin Wiley, Moraga, CA (US)

(73) Assignee: Tate & Lyle Technology Limited, London (GB)

( * ) Notice: Subject to any disclaimer, the term of this patent is extended or adjusted under 35 U.S.C. 154(b) by 497 days.

This patent is subject to a terminal disclaimer.

(21) Appl. No.: 13/262,147

(22) PCT Filed: Mar. 24, 2010

(86) PCT No.: PCT/GB2010/000554
§ 371 (c)(1),
(2), (4) Date: Mar. 6, 2012

(87) PCT Pub. No.: WO2010/112813
PCT Pub. Date: Oct. 7, 2010

(65) Prior Publication Data
US 2012/0157676 A1    Jun. 21, 2012

Related U.S. Application Data

(60) Provisional application No. 61/164,735, filed on Mar. 30, 2009.

(51) Int. Cl.
*C07C 209/86* (2006.01)
*C07H 1/06* (2006.01)
*C07H 5/02* (2006.01)

(52) U.S. Cl.
CPC ........................................ *C07H 5/02* (2013.01)
USPC ...................... 536/123.13; 564/497

(58) Field of Classification Search
CPC ............... C07H 5/02; C07H 3/04; A61K 8/60
USPC ...................... 536/123.13; 564/497
See application file for complete search history.

(56) References Cited

U.S. PATENT DOCUMENTS

| | | | |
|---|---|---|---|
| 4,783,526 A | 11/1988 | O'Brien et al. | |
| 4,889,928 A | 12/1989 | Simpson | |
| 4,950,746 A | 8/1990 | Navia et al. | |
| 4,980,463 A | 12/1990 | Walkup et al. | |
| 5,023,329 A | 6/1991 | Neiditch et al. | |
| 5,034,551 A | 7/1991 | Vernon et al. | |
| 5,061,496 A * | 10/1991 | Cherukuri et al. | ................ 426/3 |
| 5,089,608 A | 2/1992 | Walkup et al. | |
| 5,298,611 A | 3/1994 | Navia et al. | |
| 5,440,026 A | 8/1995 | Khan et al. | |
| 5,470,969 A | 11/1995 | Sankey et al. | |
| 5,498,709 A | 3/1996 | Navia et al. | |
| 5,530,106 A | 6/1996 | Navia et al. | |
| 5,977,349 A | 11/1999 | Catani et al. | |
| 6,646,121 B2 | 11/2003 | El Kabbani et al. | |
| 6,809,198 B2 | 10/2004 | El Kabbani et al. | |
| 6,890,581 B2 | 5/2005 | Vernon et al. | |
| 6,939,962 B2 | 9/2005 | Clark et al. | |
| 6,943,248 B2 | 9/2005 | Catani et al. | |
| 6,998,480 B2 | 2/2006 | Catani et al. | |
| 7,049,435 B2 | 5/2006 | Catani et al. | |
| 2006/0188629 A1 | 8/2006 | Liesen et al. | |
| 2006/0205936 A1 | 9/2006 | Jia et al. | |
| 2006/0276639 A1 | 12/2006 | Fry | |
| 2007/0015916 A1 | 1/2007 | Kabbani et al. | |
| 2007/0100139 A1 | 5/2007 | Fry | |
| 2007/0160732 A1 | 7/2007 | Deshpande et al. | |
| 2007/0227897 A1 | 10/2007 | Li et al. | |
| 2007/0270583 A1 | 11/2007 | Ratnam et al. | |

FOREIGN PATENT DOCUMENTS

| | | |
|---|---|---|
| EP | 0043649 A1 | 1/1982 |
| EP | 0409549 A2 | 1/1991 |
| EP | 0708110 A2 | 4/1996 |
| WO | WO2008/091539 A1 | 7/2008 |
| WO | WO2009/087362 A2 | 7/2009 |
| WO | WO2009/118532 A1 | 10/2009 |
| WO | WO2009/124116 A1 | 10/2009 |

OTHER PUBLICATIONS

Nebesky, Tatjana, International Search Report and Written Opinion dated Aug. 12, 2010.
Nickitas-Etienne, Athina, International Preliminary Report on Patentability dated Oct. 4, 2011.
Thomson, Bill, Combined Search and Examination Report dated Feb. 24, 2010.

* cited by examiner

*Primary Examiner* — Ganapathy Krishnan
(74) *Attorney, Agent, or Firm* — RatnerPrestia

(57) ABSTRACT

A process for removing dimethylamine (DMA) before and/or during and/or after deacylation in a reaction vessel of a feed stream comprising a sucralose-6-acylate resulting from the chlorination of a sucrose-6-acylate in the presence of dimethyl formamide (DMF), wherein the deacylation is conducted at a first set of conditions of temperature, pH and pressure, the process comprising: (a) providing a side stream loop from and to the reaction vessel; (b) adjusting the conditions of one or more of temperature, pH, and pressure in the loop, and setting the flow rate through the loop, to remove DMA while minimising carbohydrate degradation.

25 Claims, 2 Drawing Sheets

PROCESS FOR REMOVING DIMETHYLAMINE

CROSS REFERENCE TO RELATED APPLICATIONS

This application is the national phase filing of international patent application No. PCT/GB2010/000554, filed 24 Mar. 2010, and claims priority of U.S. Appln. No. 61/164,735, filed 30 Mar. 2009, the entireties of which applications are incorporated herein by reference.

FIELD OF THE INVENTION

The present invention relates to a process for removal and preferably also recovery of dimethyl amine (DMA) during the manufacture of sucralose.

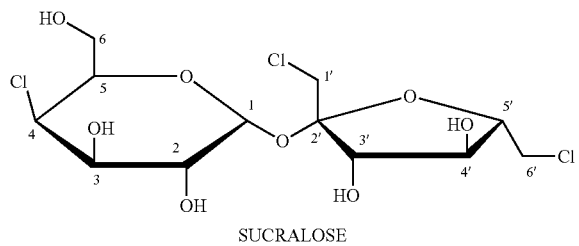

SUCRALOSE

BACKGROUND OF THE INVENTION

Sucralose is conventionally prepared by chlorination of a sucrose-6-acylate in the presence of a tertiary amide such as dimethylformamide (DMF) to form a mixture of chlorinated sucrose-6-esters, the largest component of which is 4,1',6'-trichloro-4,1',6'-trideoxy-galactosucrose-6-ester, followed by quenching at high pH, after which the DMF is removed and the acylate is hydrolysed to form crude sucralose prior to purification.

DMF is thus useful as both a solvent and a reactant during chlorination. However, cost effective manufacture depends upon recovery of this solvent from a number of streams, even when it has decomposed directly or indirectly to DMA. This recovery is economically important because of the cost of DMF and the fact that for every mole of sucralose produced, 2-20 moles of may ultimately be converted to DMA. Therefore, recovery of the solvent is very important to the economics of the process. It is also undesirable to harm/inhibit a biological waste treatment system by exposure of biomass to high levels of DMA.

It is known art to react DMA with CO under non-aqueous conditions with sodium methoxide catalyst to restore DMF. Therefore, safe and economic recovery of DMA can be used to replace costly DMF destroyed in sucralose manufacture.

The DMA is purified and concentrated by distillation and reacted with CO to reform DMF for recycle to main DMF purification systems. The separate solvent free carbohydrate waste streams can then be neutralized and treated biologically without interference by solvents.

In the case where DMA contaminates desired carbohydrate streams, careful choices must be made to preserve the carbohydrate while still freeing volatile DMA by addition of strong base, thus allowing distillation of the DMA. Where the DMA is in the presence of desirable carbohydrate, reactions can occur such as the preferable deacylation as well as undesirable decomposition of sucralose. It is thus desirable to remove and recover DMA but at the same time it is desirable to maximize the yield of sucralose by minimizing the formation of side products.

SUMMARY OF THE INVENTION

An object of the invention is to remove and preferably also recover at least part of the DMA during deacylation, or before or after deacylation, whereby deacylation occurs either prior to or following DMF stripping.

Thus, a first aspect of the present invention now provides a process for removing dimethylamine (DMA) before and/or during and/or after deacylation in a reaction vessel of a feed stream comprising a sucralose-6-acylate resulting from the chlorination of a sucrose-6-acylate in the presence of dimethyl formamide (DMF), wherein the deacylation is conducted at a first set of conditions of temperature, pH and pressure, the process comprising:
(a) providing a side stream loop from and to the reaction vessel;
(b) adjusting the conditions of one or more of temperature, pH, and pressure in the loop, and setting the flow rate through the loop, to remove DMA while minimising carbohydrate degradation.

A second aspect of the present invention provides a process of making sucralose comprising
(i) a step of removing dimethylamine (DMA) before and/or during and/or after deacylation in a reaction vessel of a feed stream comprising a sucralose-6-acylate resulting from the chlorination of a sucrose-6-acylate in the presence of dimethyl formamide (DMF), wherein the deacylation is conducted at a first set of conditions of temperature, pH and pressure, the step comprising:
(a) providing a side stream loop from and to the reaction vessel;
(b) adjusting the conditions of one or more of temperature, pH, and pressure in the loop, and setting the flow rate through the loop, to remove DMA while minimising carbohydrate degradation.
(ii) a step of isolating sucralose from the content of the reaction vessel and, optionally,
(iii) a step of purifying the isolated sucralose.

DETAILED DESCRIPTION OF THE INVENTION

Figure 1:
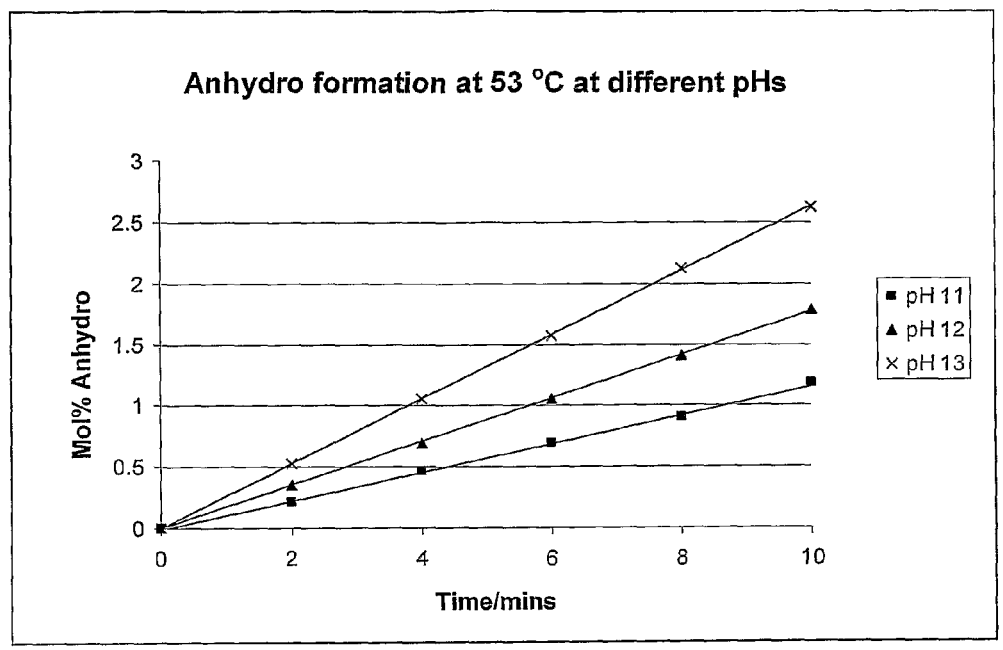
FIG. 1 is a graph showing the effect of flow rate on impurity formation at different pH values.

According to one embodiment of the present invention, the DMA removal in the side stream loop occurs substantially during the deacylation reaction. However, the DMA removal may begin before significant deacylation has begun, and after the deacylation reaction has substantially ended.

The first set of conditions for the deacylation reaction are typically as follows.

The temperature is typically from −5 to 20° C.

The pressure is typically close to atmospheric pressure, for example 760±100 torr (101.3±13.3 kPa).

The pH is typically from 9.5 to 12.5.

The feed stream for the processes of the present invention is prepared by acylation of sucrose, and chlorination, and optionally DMF removal. These procedures are described in more detail below. The method of the present invention is performed on the quenched chlorination reaction mixture.

In order to effect deacylation, the pH of the feed stream is typically raised to a level above that at which the quenching of the chlorination reaction was carried out. This can be achieved by treatment of the feed stream with a base. Any suitable base may be used, and suitable bases are those described below as the base for the quenching of the chlorination reaction. For convenience, it is preferred to use the same base for deacylation and quenching. It is particularly preferred to use sodium hydroxide as the base in both cases.

In general, the applicant has found that deacylations at higher pH values work best at relatively lower temperatures, and lower pH values work best at relatively higher temperatures. Accordingly, in some embodiments of the invention, the temperature and pressure employed for the deacylation can be selected according to the following equation:

$$T(° C.)=(-14.724)(pH)+193.52\pm 5 \text{ (or } \pm 2, \text{ in some embodiments)}$$

One or more of the conditions of temperature, pressure and pH employed for the deacylation is adjusted in the side stream loop, generally to achieve harsher conditions, for example higher temperature and/or higher pH. These harsher conditions aid DMA removal, but also may result in carbohydrate degradation, and in particular formation of "anhydro", namely 3',6'-anhydro-4,1'-dichlorogalactosucrose. The harsher conditions may also lead to further DMA formation. This effect is mitigated by reducing the exposure of the material to the conditions in the side stream loop. This can be achieved by setting the loop volume and the flow rate through the loop at any one time.

The temperature in the loop may be raised, for example, by 5-50° C., preferably by 10-40° C., more preferably by 15-20° C. The temperature may be raised, for example, to from 20 to 50° C., preferably to from 30 to 50° C., more preferably to from 40 to 50° C.

The pressure in the loop may be lowered, for example, to from 20 to 600 torr (2.7 to 80.0 kPa), preferably to from 20 torr to 80 torr (2.7 to 10.7 kPa) and still more preferably from 25 torr to 60 torr (3.3 to 8.0 kPa).

According to one embodiment of the present invention, the pH in the loop is not adjusted. Thus, adjustment of the pH in the loop is optional in the present invention.

According to another embodiment of the present invention, the pH in the loop is raised. If the pH is raised, it is preferably raised by at least 0.5 pH units, more preferably by at least 1.0 pH units. It may also be raised at least 1.5 pH units, or by at least 2.0 pH units. However, the pH in the loop is preferably raised to no higher than pH 13, more preferably to no higher than pH 12.5.

The pH may be adjusted by adding more base. The base that can be added is preferably selected from the same bases as described above for use in the deacylation reaction. The base is preferably the same as that used in the deacylation reaction.

The loop volume is the volume of the stream in the side stream loop at any one time. It is expressed as a proportion of the deacylation reaction vessel volume. The loop volume is preferably from ⅓ to 1/500 of the deacylation reaction vessel volume, more preferably from ⅕ to 1/100 of the deacylation reaction vessel volume.

"Loop volume" and "deacylation reaction vessel volume" are defined with reference to a batch-type operation for deacylation. However, the deacylation according to the present invention can be performed either as a batch process or as a continuous process. If the deacylation is performed continuously, then "volume" must be understood as "volume per unit time". The term "deacylation reaction vessel" is construed as the apparatus in which the deacylation is performed, whether deacylation is performed as a batch process or as a continuous process.

The flow rate through the loop is preferably such as to turn over from 1 to 5 volumes, preferably from 2 to 4 volumes, of the deacylation reaction vessel during the deacylation time.

According to the above parameters, the following equation can be established:

$$R=(X*V+L)/T$$

where
R=flow rate through the loop in the units of volume/time defined by V, L and T
X=number of turnovers of deacylation volume through the loop
V=deacylation reaction vessel volume
L=loop volume in the same units as V
T=total time for deacylation, or time spent performing the DMA removal in the loop.

The loop preferably comprises a condensation column. The DMA is usually removed under the conditions of reduced pressure through the condensation column.

Preferably, the loop comprises a heat exchanger heated with a heating medium disposed to heat a liquid outlet of the reaction vessel as it is fed into the loop. The temperature of the heating medium is preferably close to but not less than the target heating temperature in the loop.

Preferably, the loop comprises a heat exchanger cooled with a cooling medium disposed to cool a liquid outlet of the loop as it is fed back into the reaction vessel. The temperature of the cooling medium is preferably from -3° C. to 50° C., more preferably from 10° C. to 30° C., and still more preferably from 15° C. to 25° C.

The deacylation reaction can be conveniently monitored by HPLC. For optimum yields, it is important to monitor the progress of the deacylation reaction, and neutralise the reaction mixture when the reaction is complete. The pH of the reaction mixture should be adjusted to from 6 to 8.5, preferably approximately 7.5. The reaction mixture can conveniently be neutralised using aqueous hydrochloric acid, or using citric acid or acetic acid. Alternatively, the reaction mixture can be neutralised with gaseous carbon dioxide.

Preparation of Sucrose-6-Acylates.

Selective protection of the 6-hydroxyl of sucrose can be carried out by reaction of sucrose with a carboxylic acid anhydride, such as acetic anhydride or benzoic anhydride, in an anhydrous polar aprotic solvent (typically DMF, and, when used to prepare feed streams for the present invention, preferably DMF) in the presence of an organotin-based acylation promoter, at a temperature and for a period of time sufficient to produce the sucrose-6-ester. The 6-ester group shields the hydroxyl on the 6 position from the chlorination reaction. Accordingly, any ester group that is stable to the conditions of the chlorination reaction and which can be removed under conditions that do not affect the resulting sucralose can be used. When sucrose-6-acetate is prepared, 1,3-diacetoxy-1,1,3,3-tetrabutyldistannoxane, for example, can be used as the organotin-based acylation promoter and acetic anhydride as the carboxylic acid anhydride. Preparation of sucrose-6-esters is disclosed in, for example, O'Brien, U.S. Pat. No. 4,783,526; Navia, U.S. Pat. No. 4,950,746; Simpson, U.S. Pat. No. 4,889,928; Neiditch, U.S. Pat. No. 5,023,329; Walkup, U.S. Pat. No. 5,089,608; Vernon, U.S. Pat. No. 5,034,551; Sankey, U.S. Pat. No. 5,470,969; Kahn, U.S. Pat. No. 5,440,026; Clark, U.S. Pat. No. 6,939,962, and Li, U.S. Pat. Pub. 2007/0227897 A1; the disclosures of which are all incorporated herein by reference.

The sucrose-6-acylate can be any acylate that serves to protect the 6-hydroxy group during the chlorination reaction. It is preferably an aliphatic or carbocyclic aromatic acylate, more preferably a benzoate or acetate, and most preferably an acetate.

Chlorination of Sucrose-6-Acylates

The chlorination reaction to produce the feed streams of the present invention can be carried out by a number of methods, such as those disclosed in EP 0043649, EP 0409549, US 2006/0205936, and US 2007/0100139.

A number of chlorinating agents may be used in order to chlorinate the 4, 1' and 6' positions of the sucrose-6-acylate. Suitable examples include those selected from the group consisting of phosgene, Arnold's reagent (also known as (chloromethylene)dimethyliminium chloride or as (chloromethylene)dimethylammonium chloride), phosphorous oxychloride, phosphorous pentachloride, thionyl chloride, oxalyl chloride, methanesulfonyl chloride, sulfuryl chloride, diphosgene (trichloromethyl chloroformate) and triphosgene (bis(trichloromethyl) carbonate). Other suitable chlorinating agents known to the skilled person may also be used. Preferably, the chlorinating agent is phosgene or Arnold's reagent.

As used herein, the term "reaction vehicle" means the diluent or solvent in which the chlorination reaction is performed. The term is meant to indicate that the vehicle may not fully dissolve all the components of the reaction and product mixture. Depending on the chlorinating agent employed, a number of types of reaction vehicles may be used, and any reaction vehicle can be used that is stable under the chlorination conditions and that dissolves the starting materials, reagents, and products at least to some extent. The reaction vehicle according to the present invention comprises DMF. The ratio by weight of DMF to total carbohydrate during the chlorination reaction may be about 5:1 to about 12:1.

The reaction vehicle may additionally comprise one or more co-solvents, in addition to the tertiary amide. Suitable co-solvents are selected from the group consisting of 1,2-dichloroethane, 1,2-diethoxyethane, toluene, o-xylene, m-xylene, p-xylene, chloroform, dichloromethane, and mixtures thereof.

The chlorinating agent is preferably added in excess with respect to the sucrose-6-acylate, and preferably in large excess. At least three molar equivalents of chlorinating agent are required per mole of sucrose-6-acylate in order to chlorinate the 4, 1' and 6' positions; thus, an excess amount of chlorinating agent is any amount above three molar equivalents per mole. In a preferred embodiment, the chlorinating agent is added in an amount of at least seven molar equivalents per mole of the sucrose-6-acylate. Typically, the molar ratio of the chlorinating agent to the sucrose-6-acylate is about 7:1 to about 11:1.

A number of reaction conditions can be used to achieve the chlorination. Walkup, U.S. Pat. No. 4,980,463, the disclosure of which is incorporated herein by reference, for example, discloses a two stage process in which chlorination is carried out at two different temperatures, a temperature not higher than about 85° C. and a temperature of at least about 100° C. but not higher than about 130° C. to effect chlorination. Fry, U.S. 2007/0100139, the disclosure of which is incorporated herein by reference, discloses a process in which the reaction mixture is heated between 75° C. to 100° C. to effect chlorination.

In general, the reaction temperature for the chlorination reaction is typically from 85° C. to 130° C.

The reaction time for the chlorination depends on the temperature employed, with lower temperatures requiring longer reaction times. The skilled person can easily determine the optimum reaction time for a given reaction temperature by monitoring the reaction. If the reaction time is too short, insufficient conversion to the 4,1',6'-trichloro-4,1',6'-trideoxy-galactosucrose-6-acylate occurs. If the reaction time is too long, over-chlorination will occur, resulting in increased levels of tetra-chlorinated by-products.

Following chlorination, the process stream is quenched, for example with a base, to provide a sucralose-6-acylate and the acid salt of the base.

A number of different bases may be used in the quenching. Preferred bases for quenching include alkali metal or alkaline earth metal hydroxides, or ammonium hydroxide. As alkali metal hydroxides, sodium and potassium hydroxide are particularly suitable. As an alkaline earth metal hydroxide, calcium hydroxide is particularly suitable. The most preferred base for quenching is sodium hydroxide, due to its ready availability and low cost. Other bases known to the skilled person may also be used for quenching. The quench is preferably performed with an aqueous solution of the base. The aqueous solution may contain from about 5 wt % to about 50 wt %, typically from about 8 wt % to about 40 wt % of the base. Within these ranges, the solution of the base can be either "concentrated" or "dilute". If the solution of the base is concentrated, then precipitation of salts is envisaged, and in this case suitable concentrations are from 13 to 50 wt %, preferably from 25 to 45 wt %, more preferably about 35 wt %. If the solution of the base is dilute, precipitation of salts is not envisaged, and in that case suitable concentrations are from 5 to 15 wt %, preferably from 8 to 13 wt %, more preferably from 10 to 11 wt %.

During the quenching, the pH of the process stream should preferably be controlled, since it is generally preferred that deacylation should be minimised while quenching takes place. This pH control is readily achievable by controlling the addition rate of the aqueous solution of the base while monitoring the pH within the process stream. Any method of pH-controlled addition known to the skilled person may be used.

Suitably, the pH of the stream is maintained in the range of from about 7.5 to about 10.5 during the quenching, preferably from about 8.5 to about 10.5, more preferably from about 9.5 to about 10, more preferably from about 9.5 to about 9.75. Optionally, the pH may be maintained at a lower level, for example about 4.5, during the addition, and then raised to the preferred pH when all of the base has been added. If deacylation is to be carried out as a separate step, a pH of more than about 10 should generally be avoided during quenching, though, since deacylation may then occur. In order to avoid local extremes of pH, the reaction mixture should be adequately mixed throughout the quenching procedure.

The temperature of the stream during quenching may suitably be maintained in the range of from above 0° C. to about 80° C., for example, in the range of from 10° C. to 60° C., with a range of from about 12° C. to about 35° C. being preferred.

The quench is preferably conducted by the "dual stream quench" method, which is described in U.S. Pat. Nos. 5,530,106 and 5,498,709.

In the dual stream process, the quenching conditions are attained by slow addition of the aqueous base with simultaneous slow addition of feed material into a reaction vessel. The reaction vessel can contain an initial charge of an aqueous solution of the tertiary amide such as DMF. Slow addition of aqueous base and feed material allows both the pH and the temperature to be controlled during addition. The feed material and aqueous base are simultaneously added slowly until the desired quantity of feed material has been added. Further aqueous base is added until the desired pH is reached. Then the temperature and pH are maintained at the desired levels for the remainder of the reaction. Preferably, the pH should not be permitted to rise above about 10.5 during the course of the quenching reaction.

Quenching may alternatively be carried out by a circulated process. In the circulated process, the quenching conditions are attained by circulating feed mixture from a vessel through a circulation loop. Feed mixture and aqueous base are added slowly into this circulation loop. Slow addition of aqueous base and feed material allows both the pH and the temperature to be controlled during addition. Sufficient aqueous base is added until the desired pH is reached. Then the temperature and pH are maintained at the desired levels for the remainder of the reaction. This process may be run in a batch or continuous mode. Preferably, the pH should not be permitted to rise above about 10.5 during the course of the quenching reaction.

Following quenching, the reaction mixture may be neutralised by the addition of aqueous acid, for example aqueous hydrochloric acid. Alternatively, the reaction mixture can be taken to deacylation without prior neutralisation.

DMF Removal

The combined deacylation/DMA removal according to the present invention can be performed directly on the quenched chlorination reaction mixture, or DMF can be removed before the deacylation/DMA removal.

DMF can, if desired, be removed from the quenched chlorination reaction mixture prior to deacylation. This DMF removal can be carried out by means known in the art, such as distillation, distillation under reduced pressure, steam distillation, steam stripping, or by use of an agitated thin film drier or spray drier. It is preferred that the removal of the DMF is carried out by steam stripping. Such steam stripping can be carried out as described in EP 0708110, the disclosure of which is incorporated herein by reference.

Alternatively, DMF can be removed prior to chlorination quench. This procedure is described in co-pending U.S. provisional application Nos. 61/164,075 filed 27 Mar. 2009, and 61/164,703, filed 30 Mar., 2009, the disclosures of which are incorporated herein by reference.

DMF can also be removed after the deacylation/DMA removal according to the present invention. Processes where DMF removal is performed after deacylation are disclosed in co-pending U.S. provisional application Ser. No. 61/039,616 and PCT application no. PCT/GB2009/000006, the disclosures of which are incorporated herein by reference.

Purification of Sucralose

According to some embodiments of the present invention, sucralose is isolated following deacylation/DMA removal according to the present invention.

Methods for isolating and/or purifying sucralose, are disclosed in U.S. Pat. Nos. 6,890,581 5,977,349, 6,943,248, 6,998,480, 7,049,435, 6,809,198, 6,646,121, 5,298,611, 5,498,709, US2006/0188629, US2006/0276639, US2007/0015916, US2007/0160732, and US2007/0270583, the disclosures of which are all incorporated herein by reference.

Purification methods include liquid/liquid extraction, crystallisation, chromatography, and combinations of these. The present invention will now be explained in more detail by way of the following description of preferred embodiments and examples with reference to the accompanying drawings, in which:

FIG. 1 of the accompanying drawings show the effect of flow rate on impurity formation at different pH values.

Figure 2:
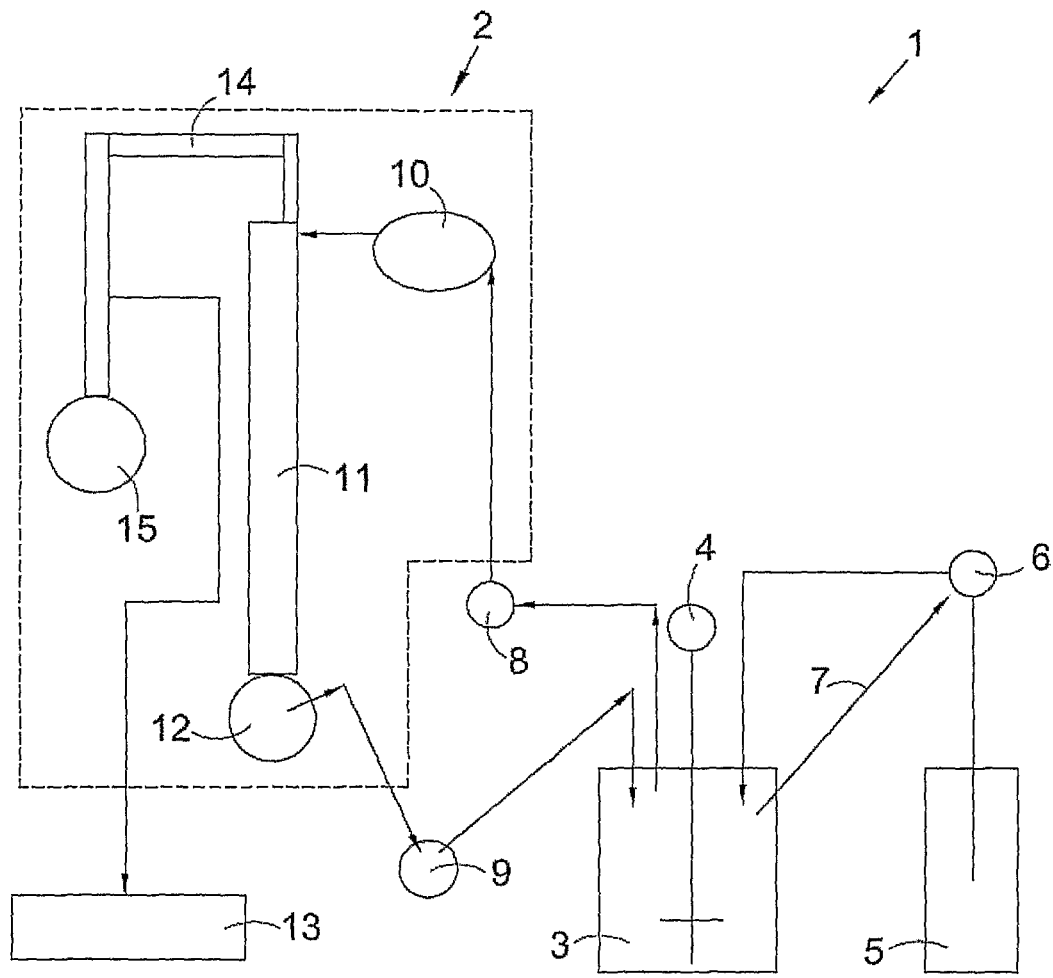
FIG. 2 is a schematic diagram showing an apparatus for use in one embodiment of the present invention.

FIG. 2 of the accompanying drawings is a schematic diagram showing an apparatus for use in one embodiment of the present invention A main purpose of carrying out the process of the invention is to convert the DMA removed from the stripping vessel to DMF. This can be achieved by reaction with CO under non-aqueous conditions using a sodium methoxide catalyst, as is known in the art. Preferably then, the DMF is recycled to be used in at least one earlier process stage, especially an earlier process stage which comprises the chlorination of the sucrose-6-acylate. Preferably also, the at least one earlier process stage comprises the acylation of the 6-hydroxy group of sucrose.

Preferred acylates comprise the acetate and the benzoate. Preferably, the deacylation is effected in the presence of one or more hydroxides selected from ammonium hydroxide and metal hydroxides, preferably alkali metal or alkaline earth metal hydroxides, especially sodium hydroxide and mixtures thereof.

Generally speaking, a non-limiting outline of the DMA removal is as follows:

1) DMAHCl is the salt form: as the pH of the medium is increased the % DMA increases. DMA may be removed by increasing the pH above 11, although any pH above which there is DMA in the free form is possible, ie: above pH 8. However, the amount of DMA removal as the pH falls below about pH 10 diminishes progressively. A vacuum is applied to the medium in the side stream loop to strip off the DMA, and preferably the temperature is also raised to volatilise the DMA.

2) Preferably, the removal process is completed in the presence of sucralose or sucralose-6-acylate. Thus, one notable advantage of the process of the present invention is that it has minimal negative impact on yield. Partial removal of DMA is possible by applying reduced pressure during high pH deacylation conditions at a temperature designed primarily to maximize sucralose yield. The remainder of the DMA must be removed by other means, such as liquid/liquid extraction followed by high pH distillation. However, if a side stream from a deacylation is looped through a brief heating and low pressure treatment in a stripping vessel (e.g. a condensation column), the efficiency of DMA removal is optimized while maintaining optimum carbohydrate deacylation conditions in the bulk solution.

3) A combination of at least one of pressure, temperature, flow rate and optionally also pH has been found during the deacylation of sucralose-6-acylate that gives high yield and high DMA removal. Surprisingly, according to one embodiment of the present invention, it has been found that it is possible to successfully strip DMA even at temperatures over 50° C., for example 53° C., so long as the residence time in the stripping column is kept to a minimum. The yield loss is greatest at higher pHs, but pHs between 11 and 13 are especially preferred for stripping the DMA, provided the residence time is kept short.

FIG. 1 of the accompanying drawings shows the effect of flow rate on anhydro (3',6'-anhydro-4,1'-dichlorogalactosucrose) formation at different pH values.

The experiments were run using quenched chlorination mass from the chlorination of sucrose-6-acetate, in which the deacetylation conditions were maintained appropriate in the main mass while a side stream was circulated briefly through a heater applying about 50° C. and exposed to vacuum in order to strip the DMA. DMA removals of 90-95% were achieved with loss of less than 2% of potential sucralose-forming carbohydrates to decomposition products.

The DMF/DMA/water streams so obtained were distilled to concentrate the DMA stream for reconversion to DMF. DMF may be similarly separated and concentrated directly for reuse.

A very wide range of deacetylation conditions have been explored, with an inverse relationship between temperature and pH. Deacetylations have been run with near 0° C. with pH as high as 13.0. Conversely, warm temperatures (40° C.) at moderate pH≥10.0 were used to achieve successful deacetylations. With a loop configuration whereby a portion of the deacetylating solution is circulated to a heated, reduced pressure loop, conditions can be obtained which will allow both good deacetylation yield and DMA removal. Lower temperatures at high pH for deacetylation give best DMA removal when briefly heated to high temperature and subjected to low pressure following return to the cooled deacetylation pot. This is due to the freeing of DMA from salts at higher pH. It is found that 50° C. is a useful temperature for the DMA strip loop. It is expected that lower temperatures (as low as 20° C.) may be employed, though requiring more aggressive vacuum and condensation. Higher temperatures are also possible, easily up to 60° C. It may be possible that even higher temperatures are possible with very brief exposure times.

Lower pressure at the DMA stripping vessel is preferable to impart impetus to remove DMA. 30-50 torr has proven to be successful, but even lower pressure, where practicable, would be helpful. Higher pressures are possible, especially if the deacetylation vessel could be pressurized.

FIG. 2 of the accompanying drawings is a schematic diagram showing an apparatus 1 for use in one embodiment of the present invention. In this embodiment, the temperature is raised and the pressure is reduced in the side stream loop 2. The pH is not, according to this embodiment, adjusted. The deacylation reaction takes place in the deacylation reaction vessel 3, which is stirred by agitator 4. The pH in the deacylation reaction vessel 3 is controlled by addition of sodium hydroxide solution from vessel 5, via pump 6. The addition of sodium hydroxide is controlled in response to the measured pH 7 inside the reaction vessel 3. A portion of the deacylation reaction mass is circulated using pumps 8 and 9 through the side stream loop 2. On entering the loop via pump 8, the stream is heated via heat exchanger 10, and then fed into column 11. The falling stream is captured in sump 12, and fed back into the deacylation reaction vessel 3 via pump 9. The deacylation reaction vessel 3 is temperature controlled. This can be achieved using a heating/cooling jacket (not shown), and/or by cooling the returning stream entering the reaction vessel 3 using a heat exchanger (not shown). The pressure in the column 11 is reduced by means of vacuum pump 13. The volatilised DMA is condensed using condenser 14, and collected via scrubber 15.

The present invention will now be explained in more detail with reference to the following non-limiting examples.

EXAMPLES

Example 1

The feed stream came from the chlorination of sucrose-6-acetate with phosgene/dimethylformamide, after quenching with sodium hydroxide solution. Such a feed stream can be produced, for example, by the methods disclosed in EP 0 409 549.

A typical composition of the feed stream from the quenched chlorination reaction is as follows:

| Description | % of total |
| --- | --- |
| Water | 49% |
| Dimethylformamide | 32% |
| Sodium chloride | 8% |
| Dimethylammonium hydrochloride | 4% |
| Sucralose-6-acetate | 3% |
| Sodium acetate | 1% |
| Others | 3% |

600 g quenched chorination mass was deacetylated over 6 hours using 15% NaOH. The reactor was jacketed and maintained at 11° C. pH 12.4 while 5 g/min was pumped through a heat exchanger having a heating medium at 53° C. (¼" diameter stainless steel coiled tube immersed in an oil bath controlled to 53° C.) and into the top of a 1" diameter column of 1 foot length at 40 torr pressure. The material was collected at the bottom of the column and pumped back to the reactor through a heat exchanger (an 8" long ¼" diameter jacketed stainless steel tube) maintained with a cooling medium at 10° C. 100% of the DMA was removed. The molar ratio of decomposition products plus unreacted sucralose-6-acetate to total potential yield reflects a loss ratio which should approach 0 as better deacetylations are achieved. This achieved 2.66%.

Example 2

600 g quenched chlorination mass was deacetylated over 6 hours using 10% NaOH. The reactor was jacketed and maintained at 20° C. pH 11.8 while 5 g/min was pumped through a heat exchanger having a heating medium at 53° C. (¼" diameter stainless steel coiled tube immersed in an oil bath controlled to 53° C.) and into the top of a 1" diameter column of 1 foot length at 40 torr pressure. The material was collected at the bottom of the column and pumped back to the reactor through a heat exchanger (an 8" long ¼" diameter jacketed stainless steel tube) maintained with a cooling medium at 10° C. 94% of the DMA was removed. The molar loss ratio (as defined above) was 4.3%.

The invention claimed is:

1. A process for removing dimethylamine (DMA) before and/or during and/or after deacylation in a reaction vessel of a feed stream comprising a sucralose-6-acylate resulting from the chlorination of a sucrose-6-acylate in the presence of dimethyl formamide (DMF), wherein the deacylation is conducted at a first set of conditions of temperature, pH and pressure, the process comprising:
   (a) providing a side stream loop from and to the reaction vessel;
   (b) adjusting the conditions of one or more of temperature, pH, and pressure in the loop, and setting the flow rate through the loop, to remove DMA while minimising carbohydrate degradation.

2. The process according to claim 1, wherein the pressure is lowered in the loop.

3. The process according to claim 2, wherein the pressure is lowered to a value in a range from 20 to 600 torr (2.7 to 80.0 kPa) in the loop.

4. The process according to claim 1, wherein the temperature is raised in the loop.

5. The process according to claim 4, wherein the temperature is raised to a value in a range from 20 to 50° C. in the loop.

6. The process according to claim 1, wherein the pH in the loop is not adjusted.

7. The process according to claim 1, wherein the pH is raised in the loop.

8. The process according to claim 1, wherein the flow rate in the loop is set to turn over the deacylation volume from one to five times.

9. The process according to claim 1, wherein the loop comprises a condensation column.

10. The process according to claim 1, wherein the loop comprises a heat exchanger heated with a heating medium disposed to heat a liquid outlet of the reaction vessel as it is fed into the loop.

11. The process according to claim 1, wherein the loop comprises a heat exchanger cooled with a cooling medium disposed to cool a liquid outlet of the loop as it is fed back into the reaction vessel.

12. The process according to claim 11, wherein the temperature of the cooling medium is from −3° C. to 50° C.

13. The process according to claim 1, wherein the DMA removed from the stripping vessel is converted to DMF.

14. The process according to claim 13, wherein the DMF is recycled to be used in at least one earlier process stage.

15. The process according to claim 14, wherein the at least one earlier process stage comprises the chlorination of the sucrose-6-acylate.

16. The process according to claim 14, wherein the at least one earlier process stage comprises the acylation of the 6-hydroxy group of sucrose.

17. The process according to claim 1, wherein the acylate is acetate.

18. The process according to claim 1, wherein the deacylation is effected in the presence of one or more hydroxides selected from ammonium hydroxide and metal hydroxides and mixtures thereof.

19. The process according to claim 1, wherein the first set of conditions of temperature, pH and pressure comprise a temperature of from −5° C. to 20° C., and/or a pressure of 760±100 torr, and/or a pH of from 9.5 to 12.5.

20. A process of making sucralose comprising
(i) a step of removing dimethylamine (DMA) before and/or during and/or after deacylation in a reaction vessel of a feed stream comprising a sucralose-6-acylate resulting from the chlorination of a sucrose-6-acylate in the presence of dimethyl formamide (DMF), wherein the deacylation is conducted at a first set of conditions of temperature, pH and pressure, the step comprising:
(a) providing a side stream loop from and to the reaction vessel;
(b) adjusting the conditions of one or more of temperature, pH, and pressure in the loop, and setting the flow rate through the loop, to remove DMA while minimising carbohydrate degradation.
(ii) a step of isolating sucralose from the content of the reaction vessel and, optionally,
(iii) a step of purifying the isolated sucralose.

21. The process according to claim 11, wherein the temperature of the cooling medium is from 10° C. to 30° C.

22. The process according to claim 11, wherein the temperature of the cooling medium is from 15° C. to 25° C.

23. The process according to claim 1, wherein the acylate is benzoate.

24. The process according to claim 1, wherein the deacylation is effected in the presence of one or more hydroxides selected from alkali metal or alkaline earth metal hydroxides and mixtures thereof.

25. The process according to claim 1, wherein the deacylation is effected in the presence of sodium hydroxide.

* * * * *

UNITED STATES PATENT AND TRADEMARK OFFICE
CERTIFICATE OF CORRECTION

PATENT NO.        : 8,912,320 B2
APPLICATION NO.   : 13/262147
DATED             : December 16, 2014
INVENTOR(S)       : John Kerr et al.

Page 1 of 1

It is certified that error appears in the above-identified patent and that said Letters Patent is hereby corrected as shown below:

In the Claims

At Column 12, line 16, "carbohydrate degradation." should read --carbohydrate degradation,--

Signed and Sealed this
Seventh Day of April, 2015

Michelle K. Lee
*Director of the United States Patent and Trademark Office*